United States Patent
Simons et al.

(10) Patent No.: US 6,852,515 B1
(45) Date of Patent: Feb. 8, 2005

(54) STIMULATION OF ANGIOGENESIS VIA ENHANCED ENDOTHELIAL EXPRESSION OF SYNDECAN-4 CORE

(75) Inventors: Michael Simons, Chestnut Hill, MA (US); Rudiger Volk, Boston, MA (US); Arie Horowitz, Waltham, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/145,916

(22) Filed: Sep. 2, 1998

(51) Int. Cl.[7] .................. C12N 15/63; C12N 15/64; C12N 15/79; C12N 15/86; C12N 5/10
(52) U.S. Cl. ............. 435/91.41; 435/91.4; 435/320.1; 435/366; 435/372; 435/371; 435/355; 435/365.1; 435/375; 435/455; 435/456; 435/69.1; 435/325; 536/23.1; 536/23.5
(58) Field of Search .................. 435/91.4, 91.41, 435/320.1, 325, 371, 355, 365.1, 375, 455, 456, 372, 366, 69.1; 536/23.1, 23.5; 424/93.1, 93.2, 93.6

(56) References Cited

U.S. PATENT DOCUMENTS 5,486,599 A * 1/1996 Saunders et al. ........... 530/395

OTHER PUBLICATIONS

Michelle J. Stanley et al, The Journal of Biological Chemistry, Herpran Sulfate–mediated Cell Aggregation, vol. 270, No. 10, Mar. 10, 1995, 5077–5083.*

* cited by examiner

Primary Examiner—David Guzo
(74) Attorney, Agent, or Firm—David Prashker

(57) ABSTRACT

The present invention provides tangible means and methods for stimulation of angiogenesis via enhanced endothelial expression of core proteins having a syndecan-4 cytoplasmic region intracellularly. The tangible means include a prepared DNA sequence fragment having separate and individual DNA sequenced portions coding for an heparan sulfate binding extracellular domain, a central transmembrane domain, and a cytoplasmic domain coding for the syndecan-4 polypeptide. The prepared DNA sequence unitary fragment may be delivered to endothelial cells in-situ, both under in-vivo and/or in-vitro conditions, using suitable expression vectors including plasmids and viruses. The resulting transfected endothelial cells overexpress heparan sulfate binding, core proteins; and the resulting overexpression of these proteoglycan entities causes stimulation of angiogenesis in-situ.

11 Claims, No Drawings

STIMULATION OF ANGIOGENESIS VIA ENHANCED ENDOTHELIAL EXPRESSION OF SYNDECAN-4 CORE

FIELD OF THE INVENTION

The present invention is concerned generally with the stimulation of angiogenesis in-situ in living tissues and organs; and is particularly directed to the preparation and use of prepared DNA sequences and expression vectors suitable for transfection of endothelial cells in-situ such that overexpression of extracellular matrix heparin sulfate binding proteoglycans subsequently occurs in-situ.

BACKGROUND OF THE INVENTION

Angiogenesis, by definition, is the formation of new capillaries and blood vessels within living tissues; and is a complex process first recognized in studies of wound healing and then within investigations of experimental tumors. Angiogenesis is thus a dynamic process which involves extracellular matrix remodeling, endothelial cell migration and proliferation, and functional maturation of endothelial cells into mature blood vessels [Brier, G. and K. Alitalo, *Trends Cell Biology* 6: 454–456 (1996)]. Clearly, in normal living subjects, the process of angiogenesis is a normal host response to injury, and as such, is an integral part of the host body's homeostatic mechanisms.

It will be noted and appreciated, however, that whereas angiogenesis represents an important component part of tissue response to ischemia, or tissue wounding, or tumor-initiated neovascularization, relatively little new blood vessel formation or growth takes place in most living tissues and organs in mature adults (such as the myocardium of the living heart) [Folkman, J. and Y. Shing, *J. Biol. Chem.* 267: 10931–10934 (1992); Folkman, J., *Nat Med.* 1: 27–31 (1995); Ware, J. A. and M. Simons, *Nature Med.* 3: 158–164 (1997)]. Moreover, although regulation of an angiogenetic response in-vivo is a critical part of normal and pathological homeostasis, little is presently known about the control mechanisms for this process. A number of different growth factors and growth factor receptors have been found to be involved in the process of stimulation and maintenance of angiogenetic responses. In addition, a number of extracellular matrix components and cell membrane-associated proteins are thought to be involved in the control mechanisms of angiogenesis. Such proteins include SPARC [Sage etal., *J. Cell Biol.* 109: 341–356 (1989); Motamed, K. and E. H. Sage, *Kidney Int.* 51: 1383–1387 (1997)]; thrombospondin 1 and 2 respectively [Folkman, J., Nat. Med. 1: 27–31 (1995); Kyriakides et al., *J. Cell Biol.* 140: 419–430 (1998)]; and integrins $\alpha v \beta 5$ and $\alpha v \beta 3$ [Brooks et al., *Science* 24: 569–571 (1994); Friedlander et al., Science 270: 1500–1502 (1995)]. However, it is now recognized that a major role is played by heparan-binding growth factors such as basic fibrocyte growth factor (bFGF) and vascular endothelial growth factor (VEGF); and thus the means for potential regulation of angiogenesis involves the extracellular heparan sulfate matrix on the surface of endothelial cells.

Research investigations have shown that heparan sulfate core proteins or proteoglycans mediate both heparin-binding growth factor/receptor interaction at the cell surface; and that accumulation and storage of such growth factors within the extracellular matrix proper occurs [Vlodavsky et al., *Clin. Exp. Metastasis* 10: 65 (1992); Olwin, B. B. and A. Rapraeger, *J. Cell Biol.* 118: 631–639 (1992); Rapraeger, A. C., Curr. Opin. Cell Biol. 1: 844–853 (1993)]. The presence of heparin or heparan sulfate is required for bFGF-dependent activation of cell growth in-vitro [Yayon et al., *Cell* 64: 841–848 (1991); Rapraeger et al., *Science* 252: 1705–1708 (1991)]; and the removal of heparan sulfate chains from the cell surface and extracellular matrix by enzymatic digestion greatly impairs bFGF activity and inhibits neovascularization in-vivo [Sasisekharan et al., *Proc. Natl. Acad. Sci. USA* 21: 1524–1528 (1994)]. Ample scientific evidence now exists which demonstrates that any alteration of heparan sulfate (HS) chain composition on the cell surface or within the extracellular matrix which is initiated by means of an altered synthesis, or a degradation, or a substantive modification of glycosaminoglycan (GAG) chains can meaningful affect the intracellular signaling cascade initiated by the growth factor. The importance of heparan sulfate in growth factor-dependent signaling has become well recognized and established in this field.

Heparan sulfate (HS) chains on the cell surface and within the extracellular matrix are present via binding to a specific category of proteins commonly referred to as "proteoglycans". This category is constituted of several classes of core proteins, each of which serve as acceptors for a different type of glycosaminoglycan (GAG) chains. The GAGs are linear co-polymers of N-acetyl-D-glycosamine [binding heparan sulfate] or N-acetyl-D-galactosamine [binding chondroitin sulfate (CS) chains] and aoidic sugars which are attached to these core proteins via a linking tetrasaccharide moiety. Three major classes of HS-carrying core proteins are present in living endothelial cells: cell membrane-spanning syndecans, GPI-linked glypicans, and a secreted perlecan core protein [Rosenberg et al, *J. Clin. Invest.* 99: 2062–2070 (1997)]. While the perlecan and glypican classes carry and bear HS chains almost exclusively, the syndecan core proteins are capable of carrying both HS and CS chains extracellularly. The appearance of specific glycosaminoglycan chains (such as HS and/or CS) extracellularly on protein cores is regulated both by the structure of the particular core protein as well as via the function of the Golgi apparatus intracellularly in a cell-type specific manner [Shworak et al., *J. Biol. Chem.* 26: 21204–21214 (1994)].

The syndecan class is composed of four closely related family proteins (syndecan-1,-2,-3 and -4 respectively) coded for by four different genes in-vivo. Syndecans-1 and -4 are the most widely studied members of this class and show expression in a variety of different cell types including epithelial, endothelial, and vascular smooth muscle cells, although expression in quiescent tissues is at a fairly low level [Bernfield et al., *Annu. Rev. Cell Biol.* 8: 365–393 (1992); Kim et al., *Mol. Biol. Cell* 5: 797–805 (1994)]. Syndecan-2 (also known as fibroglycan) is expressed at high levels in cultured lung and skin fibroblasts, although immunocytochemically this core protein is barely detectable in most adult tissues. However, syndecan-3 (also known as N-syndecan) demonstrates a much more limited pattern of expression, being largely restricted to peripheral nerves and central nervous system tissues (although high levels of expression are shown in the neonatal heart) [Carey et al., *J. Cell Biol* 117: 191–201 (1992)]. All members of the syndecan class are capable of carrying both HS and CS chains extracellularly, although most of syndecan-associated biological effects (including regulation of blood coagulation, cell adhesion, and signal transduction) are largely thought to be due to the presence of HS chains capable of binding growth factors, or cell adhesion receptors and other biologically active molecules [Rosenberg et al., *J. Clin. Invest.* 22: 2062–2070 (1997)].

Curiously, however, very little is presently known about and relatively little research attention has been paid to the function of the syndecan core proteins in-situ. Syndecan-1 expression has been observed during development suggesting a potential role in the epithelial organization of the embryonic ectoderm and in differential axial patterning of the embryonic mesoderm, as well as in cell differentiation [Sutherland et al., *Development* 113: 339–351 (1991); Trautman et al., *Development* 111: 213–220 (1991)]. Also, mesenchymal cell growth during tooth organogenesis is associated with transient induction of syndecan-1 gene expression [Vainio et al., *Dev. Biol.* 147: 322–333 (1991)]. Furthermore, in adult living tissues, expression of syndecan-1 and syndecan-4 proteoglycans increases within arterial smooth muscle cells after balloon catheter injury [Nikkari et al., *Am. J. Pathol.* 144: 1348–1356 (1994)]; in healing skin wounds [Gallo et al., *Proc. Natl. Acad. Sci. USA* 91: 11035–11039 (1994)]; and in the heart following myocardial infarction [Li et al., *Circ. Res.* 81: 785–796 (1997)]. In the latter instances, the presence of blood-derived macrophages appears necessary for the induction of syndecan-1 and 4 gene expression. However, the effects of changes in syndecan expression on cell behavior are presently not well understood. For example, this core protein is believed to mediate bFGF binding and cell activity. Overexpression of syndecan-1 in 3T3 cells led to inhibition of bFGF-induced growth [Mali et al., *J. Biol. Chem,* 268: 24215–24222 (1993)]; while in 293T cells, overexpression of syndecan-1 augmented serum-dependent growth [Numa et al., *Cancer Res.* 5: 4676–4680 (1995)]. Furthermore, syndecan-1 overexpression showed increased inter-cellular adhesion in lymphoid cells [Lbakken et al., *J. Cell Biol* 132: 1209–1221 (1996)] while also decreasing the ability of B-lymphocytes to invade collagen gels [Libersbach, B. F. and R. D. Sanderson, *J. Biol. Chem. M:* 20013–20019 (1994)]. These ostensibly contradictory findings have merely added to the uncertainty and the disparity of knowledge regarding the effects of syndecan expression.

In comparison, the glypican core protein class is composed of five murine and human members and a Drosophila dally homologue [Rosenberg et al., *J. Clin. Invest.* 99: 2062–2070 (1997)]. Unlike syndecans, the glypican members are fully extracellular proteins attached to the cell membrane via a GPI anchor. Only one member of the class, glypican-1, is expressed in endothelial cells. Another unique feature of the glypican class of proteoglycans is that they carry substantially only heparan sulfate (HS) chains [Aviezer et al., *J. Biol. Chem.* 269: 114–121 (1994)]. Consequently, while little is presently known about the biological function of glypicans, they appear able to stimulate FGF receptor 1 occupancy by bFGF and appear able to promote biological activity for several different FGF family members [Steinfeld et al., *J. Cell Biol.* 133: 405–416 (1996)].

Finally, perlecan is the third and last class of heparan sulfate (HS)-carrying core proteins. Perlecan is a secreted proteoglycan that also has been implicated in regulation of bFGF activity [Aviezer et al., *Mol. Cell Biol,* 17: 1938–1946 (1997); Steinfeld et al., *J. Cell Biol.* 133: 405–416 (1996)]. However, little is known regarding this basal lamina proteoglycan beyond its interaction with basic fibroblast growth factor receptor.

In sum therefore, it is evident that the quantity and quality of knowledge presently available regarding glycoseaminoglycan (GAG) binding core proteins is factually incomplete, often presumptive, and in some instance apparently contradictory. Clearly the rule of specific proteoglycans as mediators under varying conditions is recognized; nevertheless, the mechanisms of action and the functional activity of the various individual classes of core proteins yet remains to be elucidated in full. Thus, while the role of proteoglycans in some manner relates to angiogenesis, there is no evidence or data known to date which clearly establishes the true functional value of proteoglycans nor which establishes a use for proteoglycans as a means for stimulating angiogenesis in-situ.

SUMMARY OF THE INVENTION

The present invention has multiple aspects and is definable in multiple contexts. A first primary aspect and definition provides a prepared DNA segment for placement in a suitable expression vector and transfection of endothelial cells in-situ such that overexpression of extracellular matrix heparan sulfate proteoglycan entities subsequently occurs in-situ, said prepared DNA segment comprising:

at least one first DNA sequence coding for the extracellular domain of a discrete proteoglycan entity that is expressed by a transfected endothelial cell in-situ, said extracellular domain first DNA sequence specifying the extracellular N-terminal portion of an expressed proteoglycan entity which is then located at and extends from the endothelial cell surface and is capable of binding heparan sulfates to form an extracellular matrix in-situ.

at least one second DNA sequence coding for the transmembrane domain of a discrete proteoglycan entity that is expressed by a transfected endothelial cell in-situ, said transmembrane domain second DNA sequence specifying the medial portion of an expressed proteoglycan entity which is then located at and extends through the endothelial cell membrane and is joined with said extracellular N-terminal portion of said expressed proteoglycan entity; and at least one third DNA sequence coding for the cytoplasmic domain of the syndecan-4 molecule in said discrete proteoglycan entity that is expressed by a transfected endothelial cell in-situ, said syndecan-4 cytoplasmic domain third DNA sequence specifying the cytoplasmic portion of an expressed proteoglycan entity which is then present within the cytoplasm of a transfected endothelial cell and is joined to said transmembrane portion and said extracellular N-terminal portion of said expressed proteoglycan entity.

A second primary aspect and definition provides a constructed expression vector for transfection of endothelial cells in-situ such that overexpression of extracellular matrix haparan sulfate proteoglycan entities subsequently occurs in-situ, said constructed expression vector comprising:

a prepared DNA segment comprised of
  (i) at least one first DNA sequence coding for the extracellular domain of a discrete proteoglycan entity that is expressed by a transfected endothelial cell in-situ, said extracellular domain first DNA sequence specifying the extracellular N-terminal portion of an expressed proteoglycan entity which is then located at and extends from the endothelial cell surface and is capable of binding heparan sulfates to form an extracellular matrix in-situ,
  (ii) at least one second DNA sequence coding for the transmembrane domain of a discrete proteoglycan entity that is expressed by a transfected endothelial cell in-situ, said transmembrane domain second DNA sequence specifying the medial portion of an expressed proteoglycan entity which is then located at and extends through the endothelial cell membrane and is joined with said extracellular N-terminal portion of said expressed proteoglycan entity, and (iii) at least one third DNA sequence coding for the cytoplasmic domain of the syndecan-4 molecule in said discrete proteoglycan entity that is expressed by a transfected endothelial cell in-situ, said syndecan-4 cytoplasmic domain third DNA sequence specifying the cytoplasmic portion of an expressed proteoglycan entity which is then present within the cytoplasm of a transfected endothelial cell and is joined to said transmembrane portion and said extracellular N-terminal portion of said expressed proteoglycan entity; and an expression vector carrying said prepared DNA segment and suitable for transfection of endothelial cells in-situ.

A third primary aspect and definition provides an in-situ transfected endothelial cell which overexpresses extracellular matrix heparan sulfate proteoglycans and positions on the proteoglycans at the cell surface, said in-situ transfected endothelial cell comprising:

a viable endothelial cell previously transfected in-situ with a constructed expression vector such that said transfected endothelial cell overexpresses discrete extracellular matrix heparan sulfate proteoglycan entities coded for by said vector, said overexpressed proteoglycan entities being comprised of (i) an extracellular N-terminal portion which is located at and extends from the transfected endothelial cell surface and which binds heparan sulfates to form an extracellular matrix in-situ, said extracellular N-terminal portion being the expressed product of at least one first DNA sequence in the constructed expression vector coding for the extracellular domain of said proteoglycan entity expressed by the transfected endothelial cell in-situ, (ii) a transmembrane medial portion which is located at and extends through the endothelial cell membrane and is joined with said extracellular N-terminal portion of said proteoglycan entity, said transmembrane medial portion being the expressed product of at least one second DNA sequence in the constructed expression vector coding for the transmembrane domain of said proteoglycan entity expressed by the transfected endothelial cell in-situ, and (iii) a syndecan-4 cytoplasmic portion present within the cytoplasm of the transfected endothelial cell which is joined to said transmembrane portion and said extracellular N-terminal portion of said proteoglycan entity, said syndecan-4 cytoplasmic portion being the expressed product of at least one third DNA sequence in the constructed expression vector coding for the cytoplasmic domain of the syndecan-4 molecule of said proteoglycan entity expressed by the transfected endothelial cell in-situ.

A fourth primary aspect, and definition provides a method for stimulating angiogenesis in-situ within a living tissue comprising vascular endothelial cells, said method comprising the steps of:

transfecting vascular endothelial cells within a living tissue with a constructed expression vector such that the resulting transfected vascular endothelial cells overexpress discrete extracellular matrix heparan sulfate proteoglycan entities coded for by said constructed expression vector, said overexpressed proteoglycan entities being comprised of (i) an extracellular N-terminal portion which is located at and extends from the transfected vascular endothelial cell surface and binds heparan sulfates to form an extracellular matrix in-situ, said extracellular N-terminal portion being the expressed product of at least one first DNA sequence in the constructed expression vector coding for the extracellular domain of said proteoglycan entity expressed by a transfected vascular endothelial cell in-situ, (ii) a transmembrane medial portion which is located at and extends through a transfected vascular endothelial cell membrane and is joined with said extracellular N-terminal portion of said proteoglycan entity, said transmembrane medial portion being the expressed product of at least one second DNA sequence in the constructed expression vector coding for the transmembrane domain of said proteoglycan entity expressed by a transfected vascular endothelial cell in-situ, and (iii) a syndecan-4 cytoplasmic portion present within the cytoplasm of a transfected vascular endothelial cell which is joined to said transmembrane portion and said extracellular N-terminal portion of said expressed proteoglycan entity, said syndecan-4 cytoplasmic portion being the expressed product of at least one third DNA sequence in the constructed expression vector coding for the cytoplasmic domain of the syndecan-4 molecule of said proteoglycan entity expressed by a transfected vascular endothelial cell in-situ; and allowing said transfected vascular endothelial cells bearing said overexpressed extracellular matrix proteoglycan entities to stimulate angiogenesis in-situ.

BRIEF DESCRIPTION OF THE FIGURES

The present invention can be more easily understood and better appreciated when taken in conjunction with the accompanying drawing, in which:

FIG. 1 is a representation of a prepared DNA sequence fragment;

FIG. 2 is a recitation of the DNA sequence coding for the extracellular domain of syndecan-1[SEQ ID NO: 1];

FIG. 3 is a recitation of the DNA sequence coding for extracellular domain of syndecan-2 [SEQ ID NOS:2 & 3];

FIG. 4 is a recitation of the DNA sequence coding for the extracellular domain of syndecan-3 [SEQ ID NO:4];

FIG. 5 is a recitation of the DNA sequence coding for the extracellular domain of syndecan-4 [SEQ ID NO:5];

FIG. 6 is a recitation of the DNA sequence coding for the extracellular domain of glypican-1[SEQ ID NOS:6 & 7];

FIG. 7 is a recitation of the DNA sequence coding for the transmembrane domain of syndecan-1[SEQ ID NO:8];

FIG. 8 is a recitation of the DNA sequence coding for the transmembrane domain of syndecan-2 [SEQ ID NOS:9 & 10];

FIG. 9 is a recitation of the DNA sequence coding for the transmembrane domain of syndecan-3 [SEQ ID NO:11];

FIG. 10 is a recitation of the DNA sequence coding for the transmembrane domain of syndecan-4 [SEQ ID NO:12];

FIG. 11 is a recitation of the DNA sequence coding for the transmembrane domain of GP1 [SEQ ID NOS:13 & 14];

FIG. 12 is a recitation of the DNA sequence coding for the transmembrane domain of perlecan [SEQ ID NO:15];

FIG. 13 is a recitation of the DNA sequence coding for the cytoplasmic domain of syndecan-4 [SEQ ID NO:16];

FIG. 14 is a graph illustrating the in-vitro growth assays of ECV-derived cell clones;

FIGS. 15A–15C are photographs showing the results of Matrigel growths assays;

FIG. 16 is a graph illustrating the effect of syndecan construct expression on endothelial cell migration in Boyden chamber assays;

FIGS. 17A–17F are photographs showing BudR uptake in opiop homozygous (−1−) and heterozygous (+1−) mice;

FIG. 18 is a photograph showing Northern blot analysis of gene expression in PR-39 transgenic mice; and FIG. 19 is a graph illustrating in-vitro microvascular reactivity in PR-39 transgenic mice.

DETAILED DESCRIPTION OF THE INVENTION

The present invention provides both the tangible means and the methods for causing an overexpression of extracellular, heparan sulfate carrying, proteoglycans on-demand at and through the surface of endothelial cells; and via such on-demand overexpression of proteoglycans to stimulate angiogenesis in-situ. The tangible means include a prepared DNA segment comprising sequences coding for an extracellular domain, a transmembrane domain, and the cytoplasmic domain of the syndecan-4 protein; as well as a constructed expression vector for the transfection of endothelial cells in-situ such that overexpression of extracellular matrix, heparan sulfate bearing, proteoglycan entities subsequently occurs in-situ. The resulting transfected endothelial cell overexpresses proteoglycans and positions them at the cell surface —thereby providing the structural and functional entities by which to stimulate angiogenesis in-situ.

A number of major benefits and advantages are therefore provided by the means and methods comprising the present invention. These include the following:

1. The present invention provides in-situ stimulation for angiogenesis. By definition, therefore, both in-vivo and in-vitro circumstances of use and application are envisioned and expected. Moreover, the endothelial cells which are to be transfected such that overexpression of proteoglycans subsequently occurs, may be alternatively isolated endothelial cells, be part of living tissues comprising a variety of other cells such as fibrocytes and muscle cells, and may also comprise part of specific organs in the body of a living human or animal subject. While the user shall choose the specific conditions and circumstances for practicing the present invention, the intended scope of application and the envisioned utility of the means and methods described herein apply broadly to living cells, living tissues, functional organs and systems, as well as the complete living body unit as a viable whole.

2. The present invention has a variety of different applications and uses. Of clinical and medical interest and value, the present invention provides the opportunity to stimulate angiogenesis in tissues and organs in a living subject which has suffered defects or has undergone anoxia or infarction. A common clinical instance is the myocardial infarction or chronic myocardial ischemia of heart tissue in various zones or areas of a living human subject. The present invention thus provides opportunity and means for specific site stimulation and inducement of angiogenesis under controlled conditions. The present invention also has major research value for research investigators in furthering the quality and quantity of knowledge regarding the mechanisms controlling angiogenesis under a variety of different conditions and circumstances.

3. The present invention envisions and permits a diverse range of routes of administration and delivery means for introducing a constructed expression vector to a specific location, site, tissue, organ, or system in the living body. A variety of different expression vectors are available to the practitioner; and a diverse and useful range of delivery systems which are conventionally available and in accordance with good medical practice are adapted directly for use. In this manner, not only are the means for transfection under the control of the user, but also the manner of application and limiting the locale or area of intentional transfection of endothelial cells can be chosen and controlled.

4. The user also has the choice and discretion of the manner in which the DNA segment is prepared —so long as the prepared DNA fragment conforms to the minimal requirements set forth herein. Thus, the prepared DNA sequence fragment may comprise the entire syndecan-4 DNA sequence in each of the required extracellular, transmembrane, and cytoplasmic domains. However, it is expected and envisioned that the more frequent choice will be a chimera core protein structure which comprises only the syndecan-4 cytoplasmic domain but incorporates transmembrane and extracellular domains which are not native to the DNA of syndecan-4. Thus, the majority of prepared DNA sequenced fragments will be chimeric DNA segments ligated together intentionally using recombinant techniques and methods to form a unitary DNA fragment.

5. The present invention provides a unique capability and control for stimulating angiogenesis in-situ by genetic manipulation of the endothelial cells as they exist within the tissues and organs as found. This level of gene control and utilization of the expression mechanisms found within the cytoplasms of the endothelial cells themselves provides a point of intentional intervention which harnesses and utilizes the cellular systems of the endothelial cells themselves to produce the intended and desired result. The transfected endothelial cells in-situ are thus minimally altered from their original genetic constituents; and the methodology utilizes the natural regulatory and protein producing systems of the endothelial cells themselves to provide the overexpression of proteoglycans which are located and positioned in the normally expected manner by the endothelial cells as part of the normal homeostatic mechanisms.

Accordingly, by the very requirements of the present invention it is thus important, if not essential, that the user be at least familiar with the many techniques for manipulating and modifying nucleotides and DNA fragments which have been reported and are today widespread in use and application. Merely exemplifying the many authoritative texts and published articles presently available in the literature regarding genes, DNA nucleotide manipulation and the expression of proteins from manipulated DNA fragments are the following: *Gene Probes for Bacteria* (Macario and De Marcario, editors) Academic Press Inc., 1990; *Genetic Analysis, Principles Scope and Objectives* by John R. S. Ficham, Blackwell Science Ltd., 1994; Recombinant DNA Methodology II(Ray Wu, editor), Academic Press, 1995; Molecular Cloning, A Laboratory Manual(Maniatis, Fritsch, and Sambrook, editors), Cold Spring Harbor Laboratory, 1982; PCR(*Polymerase Chain Reaction*), (Newton and Graham, editors), Bios Scientific Publishers, 1994; and the many references individually cited within each of these publications. All of these published texts are expressly incorporated by reference herein.

In addition, a number of issued U.S. Patents and published patent applications have been issued which describe much of the underlying DNA technology and many of the conventional recombinant practices and techniques for preparing DNA sequences coding for core proteins such as syndecan-4. Merely exemplifying some of the relevant patent literature for this subject are: U.S. Pat. Nos. 5,486,599; 5,422,243; 5,654,273; 4,356,270; 4,331,901; 4,273,875; 4,304,863; 4,419,450; 4,362,867; 4,403,036; 4,363,877; as well as Publications Nos. WO9534316-A1; WO9412162-A1; WO9305167-A1; WO9012033-A1; WO9500633; WO9412162; and RO9012033. All of these patent literature publications are also expressly incorporated by reference herein.

I. Constructed Core Protein DNA Fragments

A primary component part of the subject matter as a whole comprising the present invention is the manufacture and proper use of a prepared DNA segment intended for placement in a suitable expression vector; and useful for transfection of endothelial cells in-situ, under both in-vivo and in-vitro conditions, such that overexpression of extracellular matrix heparan sulfate carrying proteoglycans subsequently occurs in-situ. The prepared DNA segment is a manufactured or synthesized nucleotide fragment which preferably exists as a single, coiled strand of DNA bases in series; and constitutes sufficient DNA information to code for three requisite domains as illustrated by FIG. 1.

FIG. 1 is a simplistic and broadly representational illustration of the prepared DNA fragment after manufacture or synthesis. As seen therein, the prepared DNA segment comprises at least a first DNA sequence coding for the extracellular domain of a discrete and identifiable proteoglycan entity which, after being expressed by a transfected endothelial cell in-situ, yields a specified N-terminal portion of an expressed proteoglycan entity. This N-terminal portion is the extracellular region of the expressed proteoglycan molecule which is then located at and extends from the transfected endothelial cell surface. This extended, extracellular N-terminal region (expressed as specific amino acid residues in sequence) is capable of binding heparan sulfates at the cell surface thereby forming an extracellular heparan sulfate matrix in-situ.

The prepared DNA segment fragment illustrated by FIG. 1 must also provide at least one se on d DNA sequence coding for the transmembrane domain of a discrete proteoglycan entity that is expressed by a transfected endothelial cell in-situ. This transmembrane domain second DNA sequence codes for and specifies the amino acid residue sequence of the medial or central portion of an expressed proteoglycan entity by the transfected endothelial cell. The medial portion or central region of the expressed proteoglycan is located at and extends through the endothelial cell membrane and is directly joined with and to the extracellular N-terminal portion of the expressed proteoglycan then extending from the cell surface.

The final requisite component of the prepared DNA segment illustrated by FIG. 1 comprises at least one third DNA sequence coding for the cytoplasmic domain of the syndecan 4 molecule within the discrete proteoglycan entity that is expressed by a transfected endothelial cell in-situ. This third DNA sequence specifies the cytoplasmic domain of the syndecan-4 DNA; and thus requires the expression of the particular amino acid residues which identify the syndecan-4 cytoplasmic region of the syndecan-4 core protein structure. While some small variation is permitted within the third DNA sequence specifying the cytoplasmic domain of the syndecan-4 amino acid structure, it is essential and required in every embodiment of the prepared DNA fragment which is the present invention that the expressed cytoplasmic region of the proteoglycan entity then present within the cytoplasm of a transfected endothelial cell be identifiably recognized as being a syndecan-4 amino acid residue type. In addition, the expressed cytoplasmic portion constituting the syndecan-4 amino acid sequence must be present within the cytoplasm of a transfected endothelial cell; and be joined to the transmembrane portion and the extracellular N-terminal portion of the expressed proteoglycan entity.

The Heterogeneous Domains Joined Together as a Unitary Fragment

It will be recognized and appreciated that the prepared DNA sequence is intended to be primarily, but not always, a heterogeneous DNA structure which joins together individual and separate DNA sequences as a unitary fragment. The cytoplasmic domain constituting the third DNA sequence of the prepared fragment is limited and restricted to those DNA bases in sequence which recognizably and identifiably code for the syndecan-4 amino acid residues. Although single point or small variant alternations or modifications in the DNA base sequence is permissible and expected, the overall domain must be in each and every instance recognizable and identifiable (using appropriate analytical means) as representative of the cytoplasmic region of the syndecan-4 molecular structure.

In comparison, the practitioner or intended user has the choice of many different DNA sequences and formats when choosing and selecting DNA sequences coding for the extracellular domain coding for the N-terminal region and the transmembrane domain coding for the central or medial region of the proteoglycan molecule to be expressed. Thus, the user may construct the entirety of the syndecan-4 DNA base sequence in its entirety such that a complete syndecan-4 core protein is subsequently expressed by a transfected endothelial cell. However, it is expected that in many instances the heterogeneous combination of individual and separate DNA base sequences representative of other and different core protein structures will be utilized; and that the resulting expressed proteoglycan entity will therefore be a chimeric core protein having different amino acid residues constituting the transmembrane region and the extracellular region of the expressed proteoglycan entity. Thus it is expected and envisioned that the first DNA sequence may be the DNA coding for the glypican-1 amino acid residues; while the second DNA sequence coding for the transmembrane domain may be representative of the syndecan-1 amino acid structure. Thus, the availability and use of heterogeneous prepared DNA fragments linking together first, second, and third DNA sequences —each of which is representative of a different core protein content and structure —thus will yield the expression of a chimeric proteoglycan entity which does not and cannot occur in nature.

In addition, the present availability of manufacturing heterogeneous DNA fragments which will yield an expressed chimera core protein in a transfected endothelial cell in-situ allows the intended user to choose and more carefully align the amino acid composition of the expressed proteoglycan entity to be in accordance with and more compatible to the particular clinical problem and specific living tissue which is the intended treatment target. Thus, if damaged myocardium is the tissue intended as the target for treatment, the manufacture of the heterogeneous fragment might include an extracellular domain (the first DNA sequence) coding for the glycipan-1 region; which is joined to the transmembrane DNA domain (the second DNA sequence) which itself codes for a syndecan-2 amino acid region; which in turn is linked to the cytoplasmic domain (the third DNA sequence) which must code for the syndecan-4 region. In comparison, however, if the targeted tissue is lung tissue, the extracellular domain might be representative of the syndecan-1 amino acid region; while the transmembrane domain represents the DNA coding for the amino acids of the syndecan-3 region; and the cytoplasmic domain continues to code exclusively for the syndecan-4 region. In other words, the extracellular domain can be specifically tailored to an environment where it will be expressed.

In this manner, the manufacturer or intended user may customize and tailor the DNA sequences constituting the extracellular domain and/or the transmembrane domain as far as possible to best meet or suit the particular tissue, clinical condition, or pathology then existing and critical to the particular application of interest. The range and variety of choices, therefore, allows the manufacturer and intended user a greater degree of flexibility, of potential therapeutic effects, and a greater degree of individuality than has ever been possible before the present invention was made.

Manufacture of the Prepared DNA Sequence Fragment

It is expected and intended that the conventionally known and commonly used recombinant DNA materials, procedures, and instrumentation will be employed for the manufacture of the prepared DNA sequence fragments. Thus, the entire prepared DNA sequence structure including the entirety of the extracellular domain and the transmembrane domain, and the cytoplasmic domain coding for the syndecan-4 structure may be synthesized directly from individual bases using the commercially available instruments and techniques. Alternatively, the DNA sequences existing in naturally occurring core proteins may be replicated; and the cDNA isolated from individual clones using the appropriate enzymes and protocols. Regardless of the methods and means of manufacture, any and all of these protocols, procedures, systems, or instruments which will yield the prepared DNA sequence as an discrete fragment is suitable and appropriate for use with the present invention.

A preferred technique, procedure, and methodology for preparing the DNA fragment as a whole is given in the Materials and Methods portion of the Experiments presented hereinafter. The described method, however, is merely one among many conventionally known and available for this purpose.

A. The Extracellular Domain DNA Sequence

The manufacturer or user has a substantial choice in the range and variety of the DNA sequences suitable for use as the extracellular domain. A representative, but non-exhaustive, listing of suitable choices is provided by Table 1 below.

TABLE 1

Representative Extracellular Domain
DNA Sequence Fragments

| Extracellular Domain Type Variant | DNA Sequence Recited By |
| --- | --- |
| syndecan-1 | FIG. 2 [SEQ ID NO:1] |
| syndecan-2 | FIG. 3 [SEQ ID NO:2] |
| syndecan-3 | FIG. 4 [SEQ ID NO:4] |
| syndecan 4 | FIG. 5 [SEQ ID NO:5] |
| glypican-1 | FIG. 6 [SEQ ID NO:6] |

B. The Transmembrane Domain DNA Sequences

The manufacturer or user also has substantial choice in the range and variety of the DNA sequences to be used as the transmembrane domain sequence coding for the medial or central region of the expressed proteoglycan entity. A representative, but non-exhaustive, listing of the second DNA sequence in the prepared fragment constituting and coding for the transmembrane domain is provided by Table 2 below.

TABLE 2

Representative Transmembrane Domain
DNA Sequence Fragments

| Transmembrane Domain Type Variant | DNA Sequence Recited By |
| --- | --- |
| syndecan-1 | FIG. 7 [SEQ ID NO:8] |
| syndecan-2 | FIG. 8 [SEQ ID NO:9] |
| syndecan-3 | FIG. 9 [SEQ ID NO:11] |
| syndecan 4 | FIG. 10 [SEQ ID NO:12] |
| GPI | FIG. 11 [SEQ ID NO:13] |
| perlecan | FIG. 12 [SEQ ID NO:14] |

C. The Cytoplasmic Domain Coding For The Syndecan-4 Peptide

The third requisite cytoplasmic domain must code for the amino acid residue structure representative of the syndecan-4 core protein. As shown experimentally by the data presented hereinafter, only the syndecan-4 cytoplasmic region and peptide structure allows for functional stimulation of angiogenesis in situ. For this reason, it is essential and required in each embodiment of the present invention that the third DNA sequence coding for the cytoplasmic domain in the expressed proteoglycan entity in a transfected endothelial cell be representative of and analytically identifiable as the syndecan-4 amino acid residue structure. A representative recitation of the DNA constituting the cytoplasmic domain of the syndecan-4 molecule is presented by FIG. 13 herein.

It will be noted and recognized that very little variability and substitution within the specific DNA base sequencing of the cytoplasmic domain of the syndecan-4 molecule is permitted. While some changes are expected, be they point mutations, block substitutions and the like, the expected or envisioned degree of variability which might be present or permitted for the cytoplasmic domain DNA is believed to be quite limited.

As representative examples: The last four amino acids (EFYA) [SEQ ID NO:25] cannot be changed or modified. Similarly, regarding the Serine residue at position 181: a mutation to an Alanine residue potentiates activation; while a mutation to Glutamate inhibits cell growth in a dominant fashion (dominant-negative mutation). Finally, the LGKKPIYKK sequences [SEQ ID NO:24] probably cannot be altered at all.

Expression Vectors And Means For Delivery In-Situ

A variety of methods are conventionally known and presently available to the user or practitioner of the present invention in order to introduce and deliver a prepared DNA sequence fragment to the intended target in-situ. The means for delivery envision and include in-vivo circumstances; ex-vivo specimens and conditions; and in-vitro culture circumstances. In addition, the present invention intends and expects that the use of the prepared DNA sequence fragment in a suitable expression vector and route of administration will be delivered to living tissues comprising endothelial cells, and typically vascular endothelial cells which constitute the basal layer of cells in capillaries and blood vessels generally. Clearly, the cells themselves are thus eukarytoic, typically mammalian cells from human and animal origin; and most typically would include the higher order mammals such as humans and domesticated animals kept as pets or sources of food intended for consumption. Accordingly, the range of animals includes all domesticated varieties involved in nutrition including cattle, sheep, pigs and the like; as well as those animals typically used as pets or raised for commercial purposes including horses, dogs, cats, and other living mammals typically living with and around humans.

Clearly, the expression vectors then must be suitable for transfection of endothelial cells in living tissues of mammalian origin and thus be compatible with that type and condition of cells under both in-vivo and/or in-vitro conditions. The expression vectors thus typically include plasmids and viruses as expression vectors.

The range and variety of plasmids suitable for use with the present invention are broadly available and conventionally known in the technical and scientific literature. A representative, but non-exhaustive, listing is provided by Table 3 below.

TABLE 3

Preferred Mammalian Plasmid Expression Vectors
Plasmid Vectors pHβ-APr-1-neo
EBO-pcD-XN
pcDNAI/amp
pcDNAI/neo
pRc/CMV
pSV2gpt
pSV2neo
pSV2-dhfr
pTk2
pRSV-neo
pMSG
pSVT7
pKo-neo
pHyg Alternatively, a wide and divergent variety of viral expression vectors suitable for insertion of the prepared DNA sequence fragment and subsequent transfection of endothelial cells in-situ is conventionally known and commonly available in this field. The particular choice of viral vector and the preparation of the fully constructed expression vector incorporating the prepared DNA sequence fragment is clearly a matter of personal convenience and choice to the intended manufacturer or user; but should be selected with a eye towards the intended application and the nature of the tissues which are the intended target. A representative, but non-exhaustive, listing of preferred viral expression vectors suitable for use as constructed vectors bearing the prepared DNA sequence fragment is provided by Table 4 below.

TABLE 4

Preferred Viral Expression Vectors

Bovine papilloma virus (BPV-1);
Epstein-Barr virus (phEBO; pREP-derived, and p205);
Retrovirus;
Adenovirus;
AAV (adeno-associated virus)
Lentivirus Clearly, both the plasmid based vectors and the viral expression vectors constitute means and methods of delivery which are conventionally recognized today as "gene therapy" modes of delivery. However, this overall approach is not the only means and method of delivery available for the present invention.

Injection of Recombinant Proteins

Intracoronary delivery is accomplished using catheter-based deliveries of recombinant human protein dissolved in a suitable buffer (such as saline) which can be injected locally (i.e., by injecting into the myocardium through the vessel wall) in the coronary artery using a suitable local delivery catheter such as a 10 mm InfusaSleeve catheter (Local Med, Palo Alto, Calif.) loaded over a 3.0 mm×20 mm angioplasty balloon, delivered over a 0.014 inch angioplasty guidewire. Delivery was accomplished by first inflating the angioplasty balloon to 30 psi, and then deliverying the protein through the local delivery catheter at 80 psi over 30 seconds (this can be modified to suit the delivery catheter).

Intracoronary bolus infusion can be accomplished by a manual injection of the protein through an Ultrafuse-X dual lumen catheter (SciMed, Minneapolis, Minn.) or another suitable device into proximal orifices of coronary arteries over 10 minutes.

Pericardial delivery is accomplished by instillation of the protein-containing solution into the pericardial sac. The pericardium is accessed either via a right atrial puncture, transthoracic puncture or via a direct surgical approach. Once the access is established, the material is infused into the pericardial cavity and the catheter is withdrawn. Alternatively, the delivery is accomplished using slow-release polymers such as heparin-alginate or ehylene vinyl acetate (EVAc). In both cases, once the protein is integrated into the polymer, the desired amount of polymer is inserted under the epicardial fat or secured to the myocardial surface using, for example, sutures. In addition, polymer can be positioned along the adventitial surface of coronary vessels.

Intramyocardial delivery can be accomplished either under direct vision following thoracotomy or using thoracoscope or via a catheter. In either case, the protein containing solution is injected using a syringe or other suitable device directly into the myocardium. Up to 2 cc of volume can be injected into any given spot and multiple locations (up to 30 injections) can be done in each patient. Catheter-based injections are carried out under fluoroscopic, ultrasound or Biosense NOGA guidance. In all cases after catheter introduction into the left ventricle the desired area of the myocardium is injected using a catheter that allows for controlled local delivery of the material.

III. Examplary Applications and Preferred Routes
Of Administration

A variety of approaches, routes of administration, and delivery methods are available using the constructed expression vector comprising an inserted DNA sequence fragment coding for a proteoglycan entity. A majority of the approaches and routes of administration described hereinafter are medical applications and specific clinical approaches intended for use with human patients having specific medical problems and pathologies. It is expected that the reader is familiar generally with the typical clinical human problem, pathology, and medical conditions described herein; and therefore will be able to follow and easily understand the nature of the intervention clinically using the present invention and the intended outcome and result of the clinical treatment —particularly as pertains to the stimulation of angiogenesis under in-vivo treatment conditions. A representative listing of preferred approaches is given by Table 5 below.

TABLE 5

Preferred Routes Of Administration

Catheter-based (intracoronary) injections and infusions;
Direct myocardial injection (intramyocardial guided);
Direct myocardial injection (direct vision-epicardial-open chest or under thorascope guidance);
Local intravascular delivery;
Liposome-based delivery;
Delivery in association with "homing" peptides.

Experimental and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

A. Materials and Methods:

Expression Constructs and Cell Culture

Immortalized ECV304 cells (ATCC, Bethesda, Md.) were cultured in Dulbecco's modified Eagle's medium (DMEM, Gibco-BRL) supplemented with heat-inactivated 10% fetal bovine serum (FBS, Gibco-BRL), 2 mM glutamine, 100 U/ml penicillin and 100 µg/ml streptomycin at 37° C. in 5% $Co_2$. Full length coding region cDNAs for rat syndecan-4 and rat glypican-1 expression constructs were prepared in a retroviral vector MSCV2.2 by cloning a BamHI/Hpa1 fragment of rat syndecan-4 into cDNA into BgLII/Eco Hpa1 fragment vector and BamH1/EcOR1 fragment of rat glypican-1 into BgLII/Eco R1 sites of the same vector. Syndecan/glypican chimeras were created via PCR mutagenesis; cloned into the pcDNA3; sequence d; and shuttled into the MSCV2.2 vector. The syndecan-4-GPI (S4-GPI) construct was created by deleting the C-terminal end of rat syndecan-4 sequence starting With $^{247}$Gln and replacing it with the C-terminal sequence of rat glypican-1 starting with $^{510}$Ser. The glypican-syndecan-4 cytoplasmic domain (G1-S4c) construct was created by replacing C-terminal sequence of rat glypican-1 starting with $^{510}$Ser with amino acids 247–321 of the rat syndecan-4 sequence. The created chimera thus contains both transmembrane and cytoplasmic regions of syndecan-4. Transfection of the MSCV2.2 vector alone was used to generate a control ECV cell population.

Retroviral transduction

The virus for transductions was produced by calcium phosphate transient transfection (29) of 10 µg of each construct on amphotropic Phoenix packaging cells (ATCC). Viral supernatants were collected after 36, 48 and 72 hrs, sterile filtered through 0.2 µm filter and then transferred to ECV-304 cells at 32° C. in the presence of 25 µg/ml DEAE-dextran. Typical viral titers in the supernatant were approximately $6-8 \times 10^5$ infectious particles/ml. Virus exposure was repeat ed 4 times for each construct; following the last exposure the cells were cultured in 10% FBS-DMEM supplemented with 400 µg/ml active G418 (Sigma) for two weeks.

Growth and Migration Assays

For growth assays, 100,000 cells were plated in 6 well cell culture plates and allowed to attach overnight. At that time, the cells were washed 3 times with phosphate-buffered saline (PBS) and the medium was changed to DMEM supplemented with 0.25% FBS. Twenty four hours later, 25 ng/ml of bFGF (Chiron Corp.) were added to the cell culture medium. Cell counts were then obtained at 24 hr intervals starting with the time of exposure to bFGF by trypsinizing the well and counting cell suspensions on a Coulter counter (Coulter Corp.).

Migration assays were carried out using modified Boyden chambers (Neuroprobe, Inc.). ECV 304 cells and derived clones were grown in 10% FBS-DMEM supplemented with 5 ng/ml DiI ($DiIC_{18}$; 1,1-dioctadecyl-3,3,3',3'-tetramethylindocarbocyanide perchlorate, Molecular Probes) living cell fluorescent stain overnight. Following that, the cells were trypsinized, washed with DMEM, diluted in DMEM supplemented with 0.5% FBS and seeded in wells at 60,000 cells per well. The cell containing compartments were separated from the lower wells by 25×80 mm polycarbonate filters with 8 µm pores (Poretics Corp.). The lower chambers were filled with 0.5% FBS-DMEM supplemented with 50 ng/ml bFGF and the entire apparatus was incubated in a tissue culture incubator at 37° C., 5% $CO_2$ for 4.5 hours. After that time non-migrating cells were removed by washing the upper wells with PBS, the upper surfaces of the filters were scraped with a plastic blade, and the filters were fixed in 4% formaldehyde for 1 min and placed on a glass slide. The migrated cells were imaged using a digital SesSys camera attached to a Nikon fluorescent microscope. For each slide, 3 non-overlapping lower power (5×) fields were selected for analysis. Following image acquisition using PMIS image processing software (Photometrics, Ltd.) the number of cells was automatically determined using Optimas 6.0 software (Bioscan, Inc.).

Matrigel Growth Assay

Growth factor depleted Matrigel (Becton Dickinson) plates were prepared by adding 0.5 ml of thawed Matrigel to a well of refrigerated 24 well tissue culture plate. The gel was allowed to solidify for one hour at 37° C. and overlaid with 1 ml of 0.5% FBS-DMEM containing 30,000 cells. The cell culture was carried out at 37° C. in a humidified atmosphere supplemented with 5% $CO_2$. The analysis of cell growth was carried out by obtaining lower (10×) and high (40×) power images of the wells with a digital SesSys camera focused on the surface of the gel using an inverted Nikon fluorescent microscope. The cell-free area was the determined using Optimas 6.0 software.

RNA Isolation and RT PCR Analysis

For RNA analysis of syndecan-4 and PR-39 expression, cell cultures were trypsinized, pelleted, and total RNA was prepared using TRI Reagent (Sigma Biosciences). The RNA pellet was dissolved in RNase-free water and ethanol precipitated. For RT-PCR analysis, 0.2 µg total RNA were used for reverse transcription with a 15 pmol of oligo$(dT)_{20}$ primer, 75 mM KCl, 3 mM $MgCl_2$, 10 mM DTT, 0.5 mM each dNTP in 50 mM Tris-HCl (pH 8.3) buffer. The mixture was heated to 70° C. for 10 min, then cooled to 37° C. while 1 µl of Super Script II reverse transcriptase (200 U/µl, Life Technologies, Inc.) was added. The reaction was allowed to proceed for 1 hr at 37° C. and then terminated by heating for 5 min followed by chilling to 4° C. 1 µl of the RT reaction mixture was used for PCR amplification using specific primers. The PCR reaction was carried out in the presence of 1.5 mM $MgCl_2$, 0.2 mM dNTP, 400 nM 3' and 5' primers and 2.5 U of Taq DNA polymerase (Boehringer Mannheim, Inc.). The following specific primers were used: Glypican-1: 5': CCC CGC CAG CAA GAG CCG GAG CT; [SEQ ID NO:18] 3': GTG AGG CTC TGG GCG AGT GGG GG, [SEQ ID NO:19] Syndecan-4: 5' (with Sac I restriction site):

ATA GAG CTC TTG GAA CCA TGG CFC CTG TCT GCC; [SEQ ID NO:20] 3': (with Eco RI restriction site): GGA ATT CCA GGT TTT ATT ATC TTT TTA TC [SEQ ID NO:21].

For standardization purposes a conserved region of human and mouse GAP-DH gene was chosen for amplification as a control template. The following primers were used: 5': CGT ATT GGG CGC. CGT GTC ACC AGG GC; [SEQ ID NO:22] 3': GGC CAT GAG CTC CAC CAC CCT GTT CG [SEQ ID NO:23]. All reactions were carried out using GeneAmp PCR 2400 system (Perkins Elmer, Inc.) as follows: 94° C. (1 min), 50–55° C. (30 sec), 72° C. (1.5 min). The additional final extension step was performed at 72° C. for 7 min. A total of 30 cycles were done for each reaction. Following PCR amplification, reaction products were subjected to 1% agarose gel electrophoresis and the amount of specific message was expressed as a ratio to GAP-DH message.

Determination of Heparan Sulfate Mass in Cultured Cells

To determine the total mass of heparan sulfate chains, endothelial cell cultures were washed twice with PBS and incubated for 24 h with 2 mCi of $Na_2^{35}SO_4$ in 2 ml of a modified basal Eagle medium supplemented with 1% Neutrodoma-SP. At the end of labeling, cells are washed with cold PBS and incubated with a lysis buffer followed by centrifugation at 15,000×g for 10 min at 4° C. Total proteoglycans (PG) are isolated from the supernatant by DEAE chromatography. Glycosaminoglycans were cleaved from the total PG pool by β-elimination and the relative content of HS and CS is determined by appropriate enzyme digests with chondroitinase ABC or Flavobactefium heparatinase 1 and 3. Preliminary experiments on microvascular endothelial cells demonstrated that the sum of HS and CS sulfate accounted for >98% of the total PG sulfate.

Scatchard Analysis of low Affinity BFGF Binding Sites

For determination of the number and affinity of bFGF heparan sulfate binding sites, endothelial cells were grown to near confluence in 24 well dishes in 10% FBS-DMEM. After two washes with cold PBS, 200 μl of binding buffer (25 mM HEPES, pH 7.4, 0.1% BSA, 0.05% gelatin in M199 medium), 6×10⁶ cpm (0.5 ng/ml) $^{25}$–1-bFGF (DuPont, specific activity 2000 C/mmol), and increasing amounts (0–600 ng/ml) cold bFGF were added to each well. The cells were incubated at 4° C. for 2 h with gentle agitation; at the end of that time, the cells were washed three times with 1 ml PBS containing 0.1% BSA and then incubated with 1% Triton-X 100 in 5 ml water supplemented with 0.01% BSA (Sigma) for 30 min at room temperature with vigorous shaking. Following this, 0.4 ml aliquots were counted in a 1272 CliniGamma counter (LKB). Cell counts determined by a Coulter Counter were employed to establish the number of cells per well. Background counts were subtracted from all samples. Scatchard analysis of the specifically bound material vs. the molar amount of cold competitor was carried out using Origin 5.0 software (Microcal Software, Inc., Northampton, Mass.). All experiments were carried in triplicate and repeated at least twice.

B. Empirical Data and Results

Experimental Series I

This series of experiments is directed to demonstrating the role of cell associated heparan sulfate chimeric core proteins in endothelial cells in-situ. The bulk of the experiments and empirical data in this series are in-vitro results.

Experiment 1:

The immortalized human endothelial cell line ECV304 was transfected with prepared retroviral constructs containing full length cDNAs for either syndecan-4 or glypican-1. In addition, in order to differentiate potential biological effects secondary to increased mass of cell surface and/or extracellular heparan sulfates versus increased core protein expression, two additional chimera core protein constructs were created. In one, S4-GPI, syndecan 4 extracellular domain was linked to the glypican 1 GPI anchored; and in another, G1-S4c, the extracellular domain of glypican 1 was linked to the transmembrane and cytoplasmic domains of syndecan-4. Cells transfected with a vector only construct (ECV-VC) were used as control. Increased expression of both syndecan-4 and glypican-1 constructs was expected to result in larger numbers of heparan sulfate chains on the cell surface.

Subsequently, the total mass of heparan sulfate chains on the wild type as well as the 4 newly generated transfected ECV cell lines was determined. Total heparan sulfate mass was significantly increased (per μg of total cellular protein) in ECV-S4, ECV-G1, ECV-S4-GPI and ECV-G1-S4c but not ECV-VC cells. This data is presented by Table E1.

In order to assess whether these changes in HS expression resulted in selective alterations of heparan binding growth factors, the low affinity binding of bFGF, a prototypical heparin binding growth factor was examined. Scatchard analysis of the wild type and newly generated transfected ECV cell lines showed that there were no significant changes in the affinity of bFGF binding (see Table E2; mean of 3 experiments). At the same time, there was a 2-fold increase in the number of bFGF binding sites in S4 and C1-S4c clones and somewhat smaller increase in ECV-G1 and ECV-S4-GPI clones (Table E2). The smaller increase in cell-associated HS mass in glypican and syndecan-4 GPI overexpressers was expected given higher shedding rates for GPI-linked glypican compared to the transmembrane syndecan. Also, the increase in the number of bFGF binding sites was of the same order as the increase in the total HS cell mass—thus showing that there was no preferential creation of bFGF binding sites and, there was no significant change in the bFGF-HS/HS ratio (calculated as ratio of a relative increase in the number of HS-bFGF sites per cell and a relative increase in the total HS mass). Thus, for a ECV-S4 clone compared to control, there was a 5.94*106/2.32*106=2.56 fold increase in the number of bFGF-HS sites (Table E2) and a 0.33/0.14=2.36 increase in the total HS mass (per Dg protein, Table E1) giving the HS-bFGF/HS ratio of 2.36/2.56=0.75.

TABLE E1

HS Mass In Various Stable Clones

| | $^{35}$S HS/g protein |
|---|---|
| ECV-VC | 0.14 ± 0.026 |
| ECV-S4 | 0.33 ± 0.042 |
| ECV-G1 | 0.23 ± 0.015 |
| ECV-S4-GPI | 0.24 ± 0.080 |
| ECV-G1-S4c | 0.34 ± 0.050 |

$^{35}$S counts in HS expressed per g of total protein.

TABLE E2

Effect of S4, G1 and chimera constructs expression on low affinity Kd and the number of binding sites for bFGF

|  | Kd | Number of sites per cell | HS-bFGF/Total HS Ratio |
| --- | --- | --- | --- |
| ECV-VC | $0.60 * 10^{-9}$ | $2.32 * 10^6$ | 1.00 |
| ECV-S4 | $0.85 * 10^{-9}$ | $5.94 * 10^6$ | 0.92 |
| ECV-G1 | $0.81 * 10^{-9}$ | $3.60 * 10^6$ | 0.95 |
| ECV-S4-GPI | $0.69 * 10^{-9}$ | $3.80 * 10^6$ | 0.96 |
| ECV-G1-S4c | $0.53 * 10^{-9}$ | $4.89 * 10^6$ | 0.87 |

Experiment 2:

To study the effect of syndecan-4 and glypican-1 expression on endothelial cell growth, the ability of wild type and newly created ECV cell lines to grow in-vitro in response to serum and bFGF was analyzed. Experimentally, all cells were growth arrested for 48 hours and then stimulated with 0.25% FBS supplemented with 25 ng/ml bFGF. The data is shown by FIG. 14 in which, V-V-vector control; G1: glypican-1 full length cDNA; S4-GPI; syndecan-4 extracellular domain linked to the GPI anchor; S4: full length syndecan-4 cDNA; G1—S4c: extracellular domain of glypican-1 linked to syndecan-4 transmembrane/cytoplasmic domain.

As shown therein, the ECV-S4 and ECV-G1—S4c cells demonstrated a 4-fold increase in cell number compared to ECV wild type or vector-transfected (MSCV) Cells. At the same time, growth of ECV-G1 or ECV-S4-GPI cells did not differ significantly from wild type ECV cells. Even though both ECV-G1 and ECV-S4-GPI clones had somewhat smaller numbers of bFGF-HS binding sites per cell, the absence of any significant change in bFGF growth response is out of proportion to the magnitude of HS-bFGF increase.

Experiment 3:

To test the effect of these constructs expression on the cells ability to form vascular structures, wild type and newly generated ECV clones were plated on Matrigel in 10% FBS-DMEM. Three days later, the presence of definable structures (cords and rings) was assayed by light microscopy. As in the case of in-vitro growth assays, ECV-S4 and ECV-G1-S4c cells formed more numerous and denser vascular structures compared to wild type ECV, ECV-G1 or ECV-S4-GPI cells. The results are shown by FIGS. 15A–15C.

As seen in FIGS. 15A–15C respectively, vector transduced ECV cells (MSCV) as well as ECV transduced with full length syndecan-4 and G1-S4c construct-carrying retroviruses were plated on growth factor depleted Matrigel supplemented with 25 ng/ml bFGF. Photographs of the gels were taken 72 hours later. Note the presence of increased vascular networks and cell density in S4 and G1-S4c panels compared to MSCV panel.

Experiment 4:

To further analyze the effect syndecan, glypican, or syndecan/glypican chimeras expression on biological behavior of endothelial cells, the migration of wild type and generated ECV cell lines migration towards serum and bFGF in Boyden chamber assays was analyzed. Similar to the growth assay results, the cell lines expressing increased amounts of syndecan-4 or glypican-syndecan-4 cytoplasmic tail chimeras demonstrated a significantly higher ability to migrate compared to wild type ECV or ECV expressing glypican-1 or extracellular domain of syndecan-4 linked to the glypican-1 GPI anchor. This is shown by FIG. 16.

Overall Conclusions:

The experiments demonstrate, therefore, that syndecan-4 expression resulted in significant increase in bFGF-stimulated growth of EC in 2-D and 3-D cultures as well as in enhanced migration towards the bFGF gradient. These results cannot be attributed to the increase in HS cell mass or preferential creation of low affinity (HS) bFGF binding sites rather than increased syndecan-4 core protein expression, since overexpression of glypican-1 while producing the same increase in HS mass did not produce increased growth and migration responses to bFGF. This conclusion is further supported by observation that while glypican-S4 cytoplasmic domain chimera closely mimicked effects of syndecan-4 overexpression, syndecan-4-GPI chimera had no effect on bFGF responses in these cells. Finally, while both syndecan-4 and glypican-1 expression increased total HS cell mass there was no significant change in the number of low or high (data not shown) affinity HS bFGF binding sites. Thus, increased expression of syndecan-4 cytoplasmic domain is associated with increased responsiveness to bFGF stimulation as defined by cell growth and migration assays.

Experimental Series II

The second experimental series is directed to demonstrating the role of climeric cone proteins in stimulating angiogenesis under in-vivo conditions. The experiments and data presented hereinafter are representative of clinical conditions and medical pathologies in living humans and animals.

Experiment 5:

To demonstrate the role and effect of chimeric cone protein in regulation of angiogenesis in-vivo, a rat myocardial infarction model [as reported in Li et al., *Am. J. Physiol.* 270: H1803-H1811 (1997)] was adapted to in-vivo studies using mice.

In this model, ligation of a proximal coronary artery leads to reproducible infarction accompanied by peri-infarction angiogenesis that can be characterized in a number of ways including in-situ hybridization, immunocytochemistry and morphometric analysis. Using this model, rapid (within 1 hour) induction of syndecan-4 gene expression in peri-infarct region that was dependent on the influx of blood-derived macrophages was demonstrated. A comparison of the extent of angiogenesis in macrophage-deficient homozygous op/op mice (low post-MI syndecan expression) to that in the op/op mice treated with GM-CSF (thus restoring macrophage population and syndecan-1/4 expression) revealed a 4 fold increase in neovascularization in the latter as determined by BudR intake and morphometric analysis. This result is shown by FIGS. 17A–17F respectively.

FIGS. 17A–17F show BudR uptake in op/op homozygous (–/–) and heterozygous (+/–) mice over 3 days time. Note the intense BudR uptake by cells on the infarct periphery in (+/–) mice but not in (–/–) mice within the per-infarct area on both day 1 and day 3 post-infarction.

Experiment 6:

To further link syndecan expression to enhanced angiogenic response in these settings, transgenic mice lines were generated with cardiac myocyte-specific expression of PR-39 peptide using A-MHC promoter. The PR-39 peptide has been shown to increase both syndecan-1 and syndecan-4 expression in-vitro in a variety of cell types. [See for example, Gallo et al., Proc. Natl. Acad. Sci. USA 91: 11035–11039 (1994) and Li et al., *Circ. Res.* 81: 785–796 (1997)].

Analysis of syndecan gene expression in PR-39 transgenic mice demonstrated marked increase in expression of syndecan-4 and glypican-1 genes. This is shown by FIG. 18. Equally important, there was no detectable expression of syndecan-1 in either wild type or transgenic mice (data not shown).

Immunocytochemical analysis with anti-CD31 antibody demonstrated increased vascular density in PR-39 transgenics and the morphometric analysis confirmed a 3 fold increase in the number of capillaries and small (<200 μm diameter) diameter vessels in these mice.

In particular, FIG. 18 shows a Northern blot analysis of gene expression in PR-39 transgenic mice. The LV myocardium from the wild type (WT) and two PR-39 transgenic lines (A,B) mice was subjected to Northern blot analysis. Note the increased syndecan-4 and glypican-1 expression in both transgenic mice compared to WT mice.

Experiment 6:

To confirm the functional significance of this increase in vascularity, the total coronary resistance was assessed in an isolated heart preparation as previously described [Li et al., J. Clin. Invest. 100: 18–24 (1997)]. In these settings, a 2 fold decrease in coronary perfusion pressure was observed for any given perfusion rate, thus confirming a reduced transmyocardial resistance to flow. To further evaluate vascular function in these mice, a study of bFGF-induced vasodilation in microvascular preparations in-vitro demonstrated an increased bFGF sensitivity of PR-39 mice vessels. This is shown by the data of FIG. 19.

As presented, FIG. 19 provides an in-vitro assessment of microvascular reactivity. Microvascular preparations from PR-39 transgenic and control mice were preconstricted with endothelium and then evaluated for a vasodilatory response to an endothelium-dependent agents ADP and bFGF. Note that while both PR-39 transgenics and controls are equally responsive to ADP, bFGF response is much more profound in the PR-39 mice (* p<0.05).

Overall Conclusions:

Myocardial-specific expression of PR-39 resulted in increased expression of syndecan-4 and glypican-1 genes that was accompanied by a functionally significant increase in coronary vascularity and enhanced bFGF responsiveness. These studies, therefore, provide rational evidence and direct support for the in-vivo efficacy of climeric cone protein expression in angiogenic stimulation.

The present invention is not to be limited in scope nor restricted in form except by the claims appended hereto.

What we claim is:

1. A prepared heterogeneous DNA segment for placement in an expression vector capable of effecting transfection of endothelial cells in-situ such that overexpression of extracellular matrix heparan sulphate proteoglycans subsequently occurs in-situ, said prepared heterogeneous DNA segment comprising:

at least one first DNA sequence coding for the extracellular domain of a recombinant proteoglycan entity that is not a naturally occurring form of a syndecan-4 molecule, and which can be expressed by a transfected endothelial cell in-situ after being transfected with an expression vector carrying said first DNA sequence, said extracellular domain first DNA sequence specifying the extracellular N-terminal portion of said expressed recombinant proteoglycan entity which then extends from the endothelial cell surface and is capable of binding heparan sulfates to form an extracellular matrix in-situ;

at least one second DNA sequence coding for the transmembrane domain of said recombinant proteoglycan entity that is not a naturally occurring form of a syndecan-4 molecule, and which can be expressed by a transfected endothelial cell in-situ after being transfected with an expression vector carrying said second DNA sequence, said transmembrane domain second DNA sequence specifying the medial portion of said expressed recombinant proteoglycan entity which then extends through the endothelial cell membrane and is joined with said extracellular N-terminal portion of said expressed recombinant proteoglycan entity; and at least one third DNA sequence coding for the cytoplasmic domain of a syndecan-4 molecule in said recombinant proteoglycan entity, and which can be expressed by a transfected endothelial cell in-situ after being transfected with an expression vector carrying said third DNA sequence, said syndecan-4 cytoplasmic domain third DNA sequence specifying the cytoplasmic portion of said expressed recombinant proteoglycan entity which is then present within the cytoplasm of a transfected endothelial cell and is joined to said transmembrane portion of said expressed recombinant proteoglycan entity.

2. The prepared heterogeneous DNA segment as recited by claim 1 wherein said first DNA sequence coding for the extracellular domain of said recombinant proteoglycan entity is selected from the group consisting of syndecan DNA sequences, glypican DNA sequences and perlecan DNA sequences.

3. The prepared heterogeneous DNA segment as recited by claim 1 wherein said second DNA sequence coding for the transmembrane domain of said recombinant proteoglycan entity is selected from the group consisting of syndecan DNA sequences, glypican DNA sequences and perlecan DNA sequences.

4. A constructed expression vector capable of effecting transfection of endothelial cells in-situ such that overexpression of extracellular matrix heparan sulfate proteoglycan subsequently occurs in-situ, said constructed expression vector comprising:

a prepared heterogeneous DNA segment comprised of (i) at least one first DNA sequence coding for the extracellular domain a recombinant proteoglycan entity that is not a naturally occurring form of a syndecan-4 molecule, and which can be expressed by a transfected endothelial cell in-situ after being transfected with an expression vector carrying said first DNA sequence, said extracellular domain first DNA sequence specifying the extracellular N-terminal portion of said expressed recombinant proteoglycan entity which then extends from the endothelial cell surface and is capable of binding heparan sulfates to form an extracellular matrix in-situ, (ii) at least one second DNA sequence coding for the transmembrane domain of said recombinant proteoglycan entity that is not a naturally occurring form of a syndecan-4 molecule, and which can be expressed by a transfected endothelial cell in-situ after being transfected with an expression vector carrying said second DNA sequence, said transmembrane domain second DNA sequence specifying the medial portion of said expressed recombinant proteoglycan entity which then extends through the endothelial cell membrane and is joined with said extracellular N-terminal portion of said recombinant proteoglycan entity, and (iii) at least one third DNA sequence coding for the cytoplasmic domain of a syndecan-4 molecule in said recombinant proteoglycan entity, and which can be expressed by a transfected endothelial cell in-situ after being transfected with an expression vector carrying said third DNA sequence, said syndecan-4 cytoplasmic domain third DNA sequence specifying the cytoplasmic portion of said expressed recombinant proteoglycan entity which is then present within the cytoplasm of a transfected endothelial cell and is joined to said transmembrane portion of said expressed recombinant proteoglycan entity; and an expression vector carrying said prepared heterogeneous DNA segment and capable of effecting transfection of endothelial cells in-situ.

5. The constructed expression vector as recited by claim 4 wherein said expression vector capable of effecting transfection of endothelial cells in-situ is a plasmid.

6. The constructed expression vector as recited by claim 4 wherein said expression vector capable of effecting transfection of endothelial cells in-situ is a virus.

7. An in-situ transfected endothelial cell which exists as a part of a living tissue in vitro, overexpresses extracellular matrix heparan sulfate recombinant proteoglycans, and positions the recombinant proteoglycans at the endothelial cell surface, said in-situ transfected endothelial cell comprising:

a viable endothelial cell transfected in-situ with a constructed expression vector such that said transfected endothelial cell overexpresses extracellular matrix heparan sulfate recombinant proteoglycan entities that are not a naturally occurring form of a syndecan-4 molecule, said overexpressed recombinant proteoglycan entities being comprised of (i) an extracellular N-terminal portion for said recombinant proteoglycan entity that is not a naturally occurring form of a syndecan-4 molecule and which extends from the transfected endothelial cell surface and binds heparan sulfates to form an extracellular matrix in-situ, said extracellular N-terminal portion being the expressed product of at least one first DNA sequence carried by the constructed expression vector and coding for the extracellular domain of said recombinant proteoglycan entity expressed by the transfected endothelial cell in-situ, (ii) a transmembrane medial portion for said recombinant proteoglycan entity that is not a naturally occurring form of a syndecan-4 molecule and which extends through the endothelial cell membrane and is joined with said extracellular N-terminal portion of said recombinant proteoglycan entity, said transmembrane medial portion being the expressed product of at least one second DNA sequence carried by the constructed expression vector and coding for the transmembrane domain of said recombinant proteoglycan entity expressed by the transfected endothelial cell in-situ, and (iii) a syndecan-4 cytoplasmic portion for said recombinant proteoglycan entity which is present within the cytoplasm of the transfected endothelial cell and is joined to said transmembrane portion of said recombinant proteoglycan entity, said syndecan-4 cytoplasmic portion being the expressed product of at least one third DNA sequence carried by the constructed expression vector and coding for the cytoplasmic domain of the syndecan-4 molecule of said recombinant proteoglycan entity expressed by the transfected endothelial cell in-situ.

8. The in-situ transfected endothelial cell as recited by claim 7 wherein said cell is selected from the group consisting of vascular endothelial cells and dermal endothelial cells.

9. The in-situ transfected endothelial cell as recited by claim 7 wherein said transfected endothelial cell exists in a tissue comprising at least one kind of muscle cell selected from the group consisting of myocardial muscle cells, smooth muscle cells and striated muscle cells.

10. A method for making a prepared heterogeneous DNA segment intended for placement in an expression vector capable of effecting transfection of endothelial cells in-situ such that overexpression of extracellular matrix heparan sulfate recombinant proteoglycan entities occurs in-situ, said method comprising the steps of:

obtaining at least one first DNA sequence coding for the extracellular domain of a recombinant proteoglycan entity that is not a naturally occurring form of a syndecan-4 molecule, and which can be expressed by a transfected endothelial cell in-situ after being transfected with an expression vector carrying said first DNA sequence, said extracellular domain first DNA sequence specifying the extracellular N-terminal portion of said expressed recombinant proteoglycan entity which then extends from the transfected endothelial cell surface and is capable of binding heparan sulfates to form an extracellular matrix in-situ;

acquiring at least one second DNA sequence coding for the transmembrane domain of said recombinant proteoglycan entity that is not a naturally occurring form of a syndecan-4 molecule, and which can be expressed by a transfected endothelial cell in-situ after being transfected with an expression vector carrying said second DNA sequence, said transmembrane domain second DNA sequence specifying the medial portion of said expressed recombinant proteoglycan entity which then extends through the transfected endothelial cell membrane and is joined with said extracellular N-terminal portion of said expressed recombinant proteoglycan entity;

procuring at least one third DNA sequence coding for the cytoplasmic domain of a syndecan-4 molecule in said recombinant proteoglycan entity, and which can be expressed by a transfected endothelial cell in-situ after being transfected with an expression vector carrying said third DNA sequence, said syndecan-4 cytoplasmic domain third DNA sequence specifying the cytoplasmic portion of said expressed recombinant proteoglycan entity which is then present within the cytoplasm of an transfected endothelial cell and is joined to said transmembrane portion of said expressed recombinant proteoglycan entity; and joining together said extracellular domain first DNA sequence, said transmembrane domain second DNA sequence, and said syndecan-4 cytoplasmic domain third DNA sequence as a prepared heterogeneous DNA segment.

11. A method for making a constructed expression vector capable of effecting transfection of endothelial cells in-situ such that overexpression of extracellular matrix heparan sulfate recombinant proteoglycan entities subsequently occurs in-situ, said method comprising the steps of:

obtaining a prepared heterogeneous DNA segment comprised of (I) at least one first DNA sequence coding for the extracellular domain of a recombinant proteoglycan entity that is not a naturally occurring form of a syndecan-4 molecule, and which can be expressed by a transfected endothelial cell in-situ after being transfected with an expression vector carrying said first DNA sequence, said extracellular domain first DNA sequence specifying the extracellular N-terminal portion of said expressed recombinant proteoglycan entity which then extends from the transfected endothelial cell surface and is capable of binding heparan sulfates to form an extracellular matrix in-situ, (ii) at least one second DNA sequence coding for the transmembrane domain of said recombinant proteoglycan entity that is not a naturally occurring form of a syndecan-4 molecule, and which can be expressed by a transfected endothelial cell in-situ after being transfected with an expression vector carrying said second DNA sequence, said transmembrane domain second DNA sequence specifying the medial portion of an expressed proteoglycan entity which then extends through the transfected endothelial cell membrane and is joined with said extracellular N-terminal portion of said expressed recombinant proteoglycan entity, and (iii) at least one third DNA sequence coding for the cytoplasmic domain of the syndecan-4 molecule in said recombinant proteoglycan entity, and which can be expressed by a transfected endothelial cell in-situ after being transfected with an expression vector carrying said third DNA sequence, said syndecan-4 cytoplasmic domain third DNA sequence specifying the cytoplasmic portion of an expressed proteoglycan entity which is then present within the cytoplasm of said transfected endothelial cell and is joined to said transmembrane portion of said expressed recombinant proteoglycan entity; and positioning said prepared heterogeneous DNA segment into an expression vector suitable for transfection of endothelial cells in-situ.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 762 base pairs
      (B) TYPE: nucleic acid
      (C) STRANDEDNESS: single
      (D) TOPOLOGY: linear (xi) SEQUENCE DESCRIPTION: SEQ ID NO: 1:

```
ATGAGACGTG CGGCGCTCTG GCTTTGGCTC TGCGCGCTGG CGCTGCGCCT GCAGCCTGCC      60

CTCCCGCAAA TTGTCACCGC AAATGTGCCT CCTGAAGACC AAGATGGCTC TGGGGACGAC     120

TCAGACAACT TCTCTGGCTC AGGCACAGGT GCTTTGCCAG ATATGACTTT GTCACGGCAG     180

ACACCTTCCA CTTGGAAGGA TGTGTGGCTC CTGACAGCTA CACCCACAGC TCCAGAACCC     240

ACCAGCAGGG ATACCGAGGC CACCCTCACC TCTATCCTGC CGGCTGGAGA GAAGCCTGAG     300

GAGGGAGAGC CCGTGGCCCA CGTGGAAGCA GAGCCTGACT TCACTGCTCG GGACAAGGAG     360

AAGGAGGCCA CCACCAGGCC TAGGGAGACC ACACAGCTCC CAGTCACCCA ACAGGCCTCA     420

ACAGCAGCCA GAGCCACCAC GGCCCAGGCA TCTGTCACGT CTCATCCCCA CGGGGATGTG     480

CAACCTGGCC TCCACGAGAC CTTGGCTCCC ACAGCACCCG GCCAACCTGA CCATCAGCCT     540

CCAAGTGTGG AGGATGGAGG CACTTCTGTC ATCAAAGAGG TTGTGGAGGA TGAAACTACC     600

AATCAGCTTC CTGCAGGAGA GGGCTCTGGA GAACAAGACT TCACCTTTGA AACATCTGGG     660

GAGAACACAG CTGTGGCTGG CGTCGAGCCT GACCTTCGGA ATCAGTCCCC AGTGGATGAA     720

GGAGCCACAG GTGCTTCTCA GGGCCTTTTG GACAGGAAGG AA                        762
```

(2) INFORMATION FOR SEQ ID NO: 2:

(i) SEQUENCE CHARACTERISTICS:
      (A) LENGTH: 1020 base pairs (B) TYPE: nucleic acid
        (C) STRANDEDNESS: single
        (D) TOPOLOGY: linear (xi) SEQUENCE DESCRIPTION: SEQ ID NO: 2:

```
GGCAGGAGGG AGGGAGCCAG AGGAAAAGAA GAGGAGGAGA AGGAGGAGGA CCCGGGGAGG    60

GAGGCGCGGC GCGGGAGGAG GAGGGGCGCA GCCGCGGAGC CAGTGGCCCC GCTTGGACGC   120

GCTGCTCTCC AGATACCCCC GGAGCTCCAG CCGCGCGGAT CGCGCGCTCC CGCCGCTCTG   180

CCCCTAAACT TCTGCCGTAG CTCCCTTTCA AGCCAGCGAA TTTATTCCTT AAAACCAGAA   240

ACTGAACCTC GGCACGGGAA AGGAGTCCGC GGAGGAGCAA AACCACAGCA GAGCAAGAAG   300

AGCTTCAGAG AGCAGCCTTC CCGGAGCACC AACTCCGTGT CGGGAGTGCA GAAACCAACA   360

AGTGAGAGGG CGCCGCGTTC CCGGGGCGCA GCTGCGGGCG GCGGGAGCAG GCGCAGGAGG   420

AGGAAGCGAG CGCCCCCGAG CCCCGAGCCC GAGTCCCCGA GCCTGAGCCG CAATCGCTGC   480

GGTACTCTGC TCCGGATTCG TGTGCGCGGG CTCGCCGAGC GCTGGGCAGG AGGCTTCGTT   540

TTGCCCTGGT TGCAAGCAGC GGCTGGGAGC AGCCGGTCCC TGGGGAATAT GCGGCGCGCG   600

TGGATCCTGC TCACCTTGGG CTTGGTGGCC TGCGTGTCGG CGGAGTCGAG AGCAGAGCTG   660

ACATCTGATA AAGACATGTA CCTTGACAAC AGCTCCATTG AAGAAGCTTC AGGAGTGTAT   720

CCTATTGATG ACGATGACTA CGCTTCTGCG TCTGGCTCGG GAGCTGATGA GGATGTAGAG   780

AGTCCAGAGC TGACAACAAC TCGACCACTT CCAAAGATAC TGTTGACTAG TGCTGCTCCA   840

AAAGTGGAAA CCACGACGCT GAATATACAG AACAAGATAC CTGCTCAGAC AAAGTCACCT   900

GAAGAAACTG ATAAAGAGAA AGTTCACCTC TCTGACTCAG AAAGGAAAAT GGACCCAGCC   960

GAAGAGGATA CAAATGTGTA TACTGAGAAA CACTCAGACA GTCTGTTTAA ACGGACAGAA  1020
```

(2) INFORMATION FOR SEQ ID NO: 3:

(i) SEQUENCE CHARACTERISTICS:
        (A) LENGTH: 340 amino acids
        (B) TYPE: amino acid
        (C) STRANDEDNESS: single
        (D) TOPOLOGY: linear (xi) SEQUENCE DESCRIPTION: SEQ ID NO: 3:

```
Gly Arg Arg Glu Gly Ala Arg Gly Lys Glu Glu Glu Lys Glu Glu
1               5                   10                  15

Asp Pro Gly Arg Glu Ala Arg Arg Gly Arg Arg Gly Ala Ala Ala
            20                  25                  30

Glu Pro Val Ala Pro Leu Gly Arg Ala Ala Leu Gln Ile Pro Pro Glu
            35                  40                  45

Leu Gln Pro Arg Gly Ser Arg Ala Pro Ala Ala Leu Pro Leu Asn Phe
    50                  55                      60

Cys Arg Ser Ser Leu Ser Ser Gln Arg Ile Tyr Ser Leu Lys Pro Glu
65              70                  75                      80

Thr Glu Pro Arg His Gly Lys Gly Val Arg Gly Gly Ala Lys Pro Gln
                85                  90                  95

Gln Ser Lys Lys Ser Phe Arg Glu Gln Pro Ser Arg Ser Thr Asn Ser
            100                 105                 110

Val Ser Gly Val Gln Lys Pro Thr Ser Glu Arg Ala Pro Arg Ser Arg
            115                 120                 125

Gly Ala Ala Ala Gly Gly Gly Ser Arg Arg Arg Arg Lys Arg Ala
            130                 135                 140

Pro Pro Ser Pro Glu Pro Glu Ser Pro Ser Leu Ser Arg Asn Arg Cys
```

```
               145                 150                 155                 160
Gly Thr Leu Leu Arg Ile Arg Val Arg Gly Leu Ala Glu Arg Trp Ala
                    165                 170                 175
Gly Gly Phe Val Leu Pro Trp Leu Gln Ala Ala Ala Gly Ser Ser Arg
                180                 185                 190
Ser Leu Gly Asn Met Arg Arg Ala Trp Ile Leu Thr Leu Gly Leu
                195                 200                 205
Val Ala Cys Val Ser Ala Glu Ser Arg Ala Glu Leu Thr Ser Asp Lys
            210                 215                 220
Asp Met Tyr Leu Asp Asn Ser Ser Ile Glu Glu Ala Ser Gly Val Tyr
225                 230                 235                 240
Pro Ile Asp Asp Asp Tyr Ala Ser Ala Ser Gly Ser Gly Ala Asp
                245                 250                 255
Glu Asp Val Glu Ser Pro Glu Leu Thr Thr Arg Pro Leu Pro Lys
                260                 265                 270
Ile Leu Leu Thr Ser Ala Ala Pro Lys Val Glu Thr Thr Thr Leu Asn
            275                 280                 285
Ile Gln Asn Lys Ile Pro Ala Gln Thr Lys Ser Pro Glu Glu Thr Asp
        290                 295                 300
Lys Glu Lys Val His Leu Ser Asp Ser Glu Arg Lys Met Asp Pro Ala
305                 310                 315                 320
Glu Glu Asp Thr Asn Val Tyr Thr Glu Lys His Ser Asp Ser Leu Phe
                    325                 330                 335
Lys Arg Thr Glu
            340

(2) INFORMATION FOR SEQ ID NO: 4:

(i) SEQUENCE CHARACTERISTICS:
        (A) LENGTH: 1079 base pairs
        (B) TYPE: nucleic acid
        (C) STRANDEDNESS: single
        (D) TOPOLOGY: linear (xi) SEQUENCE DESCRIPTION: SEQ ID NO: 4:

GCCCCCGCGC GCTGCTGAGC CGTCCTTGCG GCACGSSGAT GCCCGCGGAG CTGCGGCGCC      60
TCGCGGTGCT GCTGCTGCTG CTCAGCGCCC GCGCAGCGCT GGCTCAGCCG TGGCGCAATG     120
AGAACTACGA GAGGCCGGTG GACCTGGAGG GCTCTGGGGA TGATGATCCC TTTGGGGACG     180
ATGAACTGGA TGACATCTAC TCGGGCTCCG GCTCAGGCTA TTTTGAGCAG GAGTCAGGGT     240
TGGAGACAGC GGTCAGCCTC ACCACGGACA CGTCCGTCCC ACTGCCCACC ACGGTGGCCG     300
TGCTGCCTGT CACCTTGGTG CAGCCCATGG CAACACCCTT TGAGCTGTTC CCCACAGAGG     360
ACACGTCCCC TGAGCAAACA ACCAGCGTCT TGTATATCCC CAAGATAACA GAAGCACCAG     420
TGATCCCCAG CTGGAAAACA ACCACCGCCA GTACCACTGC CAGTGACTCC CCCAGTACCA     480
CCTCCACCAC CACCACCACG GCTGCTACCA CCACCACAAC CACCACCACC ATCAGCACCA     540
CTGTGGCCAC CTCCAAGCCC ACCACTACCC AGAGGTTCCT GCCCCCCTTT GTCACCAAGG     600
CAGCCACCAC CCGGGCCACC ACCCTGGAGA CGCCCACCAC CTCCATCCCT GAAACCAGTG     660
TCCTGACAGA GGTGACCACA TCACGGCTTG TCCCCTCCAG CACAGCCAAG CCGAGGTCCC     720
TGCCAAAACC AAGCACTTCC AGGACTGCAG AACCCACGGA AAAAGCACT GCCTTGCCTT     780
CCAGCCCCAC CACGCTGCCA CCCACAGAAG CCCCCCAGGT GGAGCCAGGG GAGTTGACGA     840
CAGTCCTCGA CAGTGACCTG GAAGTCCCAA CCAGTAGTGG CCCCAGCGGG GACTTCGAGA     900
```

```
TCCAGGAGGA GGAGGAGACA ACTCGTCCTG AGCTGGGCAA TGAGGTGGTG GCAGTGGTGA      960

CACCACCAGC AGCACCGGGG CTGGGCAAGA ATGCAGAGCC GGGGCTCATC GACAACACAA     1020

TAGAGTCGGG CAGCTCGGCT GCTCAGCTCC CCCAGAAAAA CATCCTGGAG AGGAAGGAA     1079
```

(2) INFORMATION FOR SEQ ID NO: 5:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (xi) SEQUENCE DESCRIPTION: SEQ ID NO: 5:

```
ATGGCGCCTG TCTGCCTGTT TGCGCCGCTG CTGCTGTTGC TCCTCGGAGG TTTCCCCGTC       60

GCCCCAGGCG AGTCGATTCG AGAGACTGAG GTCATAGACC CCAGGACCT CCTGGAAGGC      120

AGATACTTCT CTGGAGCCCT CCCGGACGAT GAAGACGCTG GGGGCCTTGA GCAGGACTCT      180

GACTTTGAGC TGTCGGGTTC CGGAGATCTA GATGACACGG AGGAGCCCAG GACCTTCCCT      240

GAGGTGATTT CACCCTTGGT GCCACTAGAT AACCACATCC CCGAGAATGC CCAGCCTGGC      300

ATCCGTGTCC CCTCAGAGCC CAAGGAACTG GAAGAGAATG AGGTCATTCC CAAAAGGGTC      360

CCCTCCGACG TGGGGGATGA CGATGTGTCC AACAAAGTGT CCATGTCCAG CACTTCCCAG      420

GGCAGCAACA TTTTTGAAAG AACTGAG                                        447
```

(2) INFORMATION FOR SEQ ID NO: 6:

(i) SEQUENCE CHARACTERISTICS:
        (A) LENGTH: 1590 base pairs
        (B) TYPE: nucleic acid
        (C) STRANDEDNESS: single
        (D) TOPOLOGY: linear (xi) SEQUENCE DESCRIPTION: SEQ ID NO: 6:

```
ATGGAGCTCC GGGCCCGAGG CTGGTGGCTG CTGTGCGCGG CCGCCGCGCT AGTCGCCTGC       60

GCCCGCGGGG ACCCCGCCAG CAAGAGCCGG AGCTGCAGCG AAGTCCGCCA GATCTACGGG      120

GCTAAGGGCT TTAGCCTGAG CGACGTGCCC CAGGCAGAGA TCTCGGGAGA GCACCTGCGG      180

ATCTGCCCCC AGGGCTACAC CTGCTGCACC AGTGAGATGG AGGAGAACCT GGCCAACCAC      240

AGCCGGATGG AGCTGGAGAC CGCACTCCAC GACAGCAGCC GTGCCCTGCA GGCTACACTG      300

GCCACCCAGC TGCATGGCAT CGATGACCAC TTCCAGCGCC TGCTGAATGA CTCGGAGCGT      360

ACACTGCAGG ATGCTTTTCC CGGGGCCTTT GGGGACCTGT ACACGCAGAA CACTCGGGCC      420

TTCCGGGACC TGTATGCTGA GCTGCGTCTC TACTACCGAG GGGCCAACCT ACACCTTGAG      480

GAGACACTGG CCGAGTTCTG GGCACGGCTG CTGGAGCGTC TCTTCAAGCA GCTGCACCCC      540

CAGCTTCTGC TGCCCGATGA CTATCTGGAC TGCCTGGGCA AGCAGGCAGA GGCACTGCGG      600

CCGTTTGGGG ATGCCCCTCG AGAACTGCGC CTGAGGGCCA CCCGTGCTTT TGTGGCGGCA      660

CGATCCTTTG TGCAGGGCCT GGGTGTGGCC AGTGACGTAG TCCGAAAGGT GGCCCAGGTT      720

CCTCTGGCCC CAGAATGTTC TCGGGCTGTC ATGAAGTTGG TCTACTGTGC CCATTGCCGG      780

GGAGTCCCTG GTGCCCGGCC CTGTCCCGAC TATTGCCGAA ATGTGCTCAA GGCTGCCTT      840

GCCAACCAGG CCGACCTGGA TGCCGAGTGG AGGAACCTCC TGGACTCCAT GGTGCTCATC      900

ACTGACAAGT TCTGGGGCCC GTCGGGTGCG GAGAATGTCA TTGGCAGTGT GCATATGTGG      960

CTGGCGGAGG CCATCAACGC CCTCCAGGAC AACAAGGACA CACTCACAGC TAAGGTCATC     1020

CAGGGCTGCG GAAACCCCAA GGTCAATCCC CATGGCTCTG GGCCTGAGGA GAAGCGTCGC     1080
```

```
CGTGGCAAAC TGGCACTGCA GGAGAAGTCC TCCACAGGTA CTCTGGAAAA GCTGGTCTCT    1140

GAGGCCAAGG CCCAGCTCCG AGACATTCAG GACTACTGGA TCAGCCTCCC AGGGACACTG    1200

TGTAGTGAGA AGATGGCCAT GAGTCCTGCC AGCGATGACC GCTGCTGGAA TGGGATTTCC    1260

AAGGGCCGGT ACCTACCTGA GGTGATGGGT GATGGGCTGG CCAACCAGAT CAACAACCCT    1320

GAAGTGGAGG TGGACATCAC CAAGCCGGAT ATGACCATCC GGCAGCAGAT CATGCAGCTC    1380

AAGATCATGA CCAACCGTTT ACGTGGCGCC TACGGTGGCA ATGATGTGGA CTTCCAGGAT    1440

GCCAGTGATG ACGGCAGTGG CTCCGGCAGC GGTGGCGGAT GCCCAGATGA CGCCTGTGGC    1500

CGGAGGGTCA GCAAGAAGAG CTCCAGCTCC CGGACCCCCT TGACCCATGC CCTCCCCGGC    1560

TTGTCAGAAC AGGAGGGACA GAAGACCTCG                                    1590
```

(2) INFORMATION FOR SEQ ID NO: 7:

(i) SEQUENCE CHARACTERISTICS:
        (A) LENGTH: 531 amino acids
        (B) TYPE: amino acid
        (C) STRANDEDNESS: single
        (D) TOPOLOGY: linear (xi) SEQUENCE DESCRIPTION: SEQ ID NO: 7:

```
Met Glu Leu Arg Ala Arg Gly Trp Trp Leu Leu Cys Ala Ala Ala
1               5                   10                  15

Leu Val Ala Cys Ala Arg Gly Asp Pro Ala Ser Lys Ser Arg Ser Cys
                20                  25                  30

Ser Glu Val Arg Gln Ile Tyr Gly Ala Lys Gly Phe Ser Leu Ser Asp
            35                  40                  45

Val Pro Gln Ala Glu Ile Ser Gly Glu His Leu Arg Ile Cys Pro Gln
        50                  55                  60

Gly Tyr Thr Cys Cys Thr Ser Glu Met Glu Glu Asn Leu Ala Asn His
65                  70                  75                  80

Ser Arg Met Glu Leu Glu Thr Ala Leu His Asp Ser Ser Arg Ala Leu
                85                  90                  95

Gln Ala Thr Leu Ala Thr Gln Leu His Gly Ile Asp Asp His Phe Gln
            100                 105                 110

Arg Leu Leu Asn Asp Ser Glu Arg Thr Leu Gln Asp Ala Phe Pro Gly
        115                 120                 125

Ala Phe Gly Asp Leu Tyr Thr Gln Asn Thr Arg Ala Phe Arg Asp Leu
    130                 135                 140

Tyr Ala Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Asp Ala Pro Arg Glu
        195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Ala Pro Glu Cys Ser Arg Ala Val Met Lys Leu Val Tyr Cys
                245                 250                 255

Ala His Cys Arg Gly Val Pro Gly Ala Arg Pro Cys Pro Asp Tyr Cys
```

```
              260             265             270
Arg Asn Val Leu Lys Gly Cys Leu Ala Asn Gln Ala Asp Leu Asp Ala
            275             280             285
Glu Trp Arg Asn Leu Leu Asp Ser Met Val Leu Ile Thr Asp Lys Phe
290             295             300
Trp Gly Pro Ser Gly Ala Glu Asn Val Ile Gly Ser Val His Met Trp
305             310             315             320
Leu Ala Glu Ala Ile Asn Ala Leu Gln Asp Asn Lys Asp Thr Leu Thr
            325             330             335
Ala Lys Val Ile Gln Gly Cys Gly Asn Pro Lys Val Asn Pro His Gly
            340             345             350
Ser Gly Pro Glu Glu Lys Arg Arg Gly Lys Leu Ala Leu Gln Glu
            355             360             365
Lys Ser Ser Thr Gly Thr Leu Glu Lys Leu Val Ser Glu Ala Lys Ala
    370             375             380
Gln Leu Arg Asp Ile Gln Asp Tyr Trp Ile Ser Leu Pro Gly Thr Leu
385             390             395             400
Cys Ser Glu Lys Met Ala Met Ser Pro Ala Ser Asp Asp Arg Cys Trp
                405             410             415
Asn Gly Ile Ser Lys Gly Arg Tyr Leu Pro Glu Val Met Gly Asp Gly
            420             425             430
Leu Ala Asn Gln Ile Asn Asn Pro Glu Val Glu Val Asp Ile Thr Lys
            435             440             445
Pro Asp Met Thr Ile Arg Gln Gln Ile Met Gln Leu Lys Ile Met Thr
    450             455             460
Asn Arg Leu Arg Gly Ala Tyr Gly Gly Asn Asp Val Asp Phe Gln Asp
465             470             475             480
Ala Ser Asp Asp Gly Ser Gly Ser Gly Gly Cys Pro Asp
            485             490             495
Asp Ala Cys Gly Arg Arg Val Ser Lys Ser Ser Ser Arg Thr
            500             505             510
Pro Leu Thr His Ala Leu Pro Gly Leu Ser Glu Gln Glu Gly Gln Lys
    515             520             525
Thr Ser Ala
530

(2) INFORMATION FOR SEQ ID NO: 8:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 8:

GTGCTGGGAG GTGTCATTGC TGGAGGCCTG GTGGGCCTCA TCTTTGCTGT GTGCCTGGTG         60

GCTTTCATGC TATAC                                                         75

(2) INFORMATION FOR SEQ ID NO: 9:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 9:
```

```
GTCCTAGCAG CTGTCATTGC TGGTGGAGTT ATTGGCTTTC TCTTTGCAAT TTTTCTTATC    60

CTGCTGTTGG TG                                                        72

(2) INFORMATION FOR SEQ ID NO: 10:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 10:

Val Leu Ala Ala Val Ile Ala Gly Gly Val Ile Gly Phe Leu Phe Ala
1               5                  10                  15

Ile Phe Leu Ile Leu Leu Leu Val
            20

(2) INFORMATION FOR SEQ ID NO: 11:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 11:

GTGTTGATAG CTGTGATTGT CGGCGGTGTG GTGGGAGCCC TCTTTGCTGC CTTCCTTGTC    60

ATGCTGCTCA TCTAC                                                     75

(2) INFORMATION FOR SEQ ID NO: 12:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 12:

GTCTTGGCAG CTCTGATTGT GGGCGGCGTA GTGGGCATCC TCTTCGCCGT TTTCCTGATC    60

CTGCTGCTGG TGTAC                                                     75

(2) INFORMATION FOR SEQ ID NO: 13:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (xi) SEQUENCE DESCRIPTION: SEQ ID NO: 13:

GCCGCCACTC GCCCAGAGCC TCACTACTTC TTTCTGCTCT TCCTGTTCAC CTTGGTCCTT    60

GCTGCAGCCA GGCCCAGGTG GCGGTAACTG CCC                                 93

(2) INFORMATION FOR SEQ ID NO: 14:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 14:

Ala Thr Arg Pro Glu Pro His Tyr Phe Phe Leu Leu Phe Leu Phe Thr
1               5                  10                  15
```

```
Leu Val Leu Ala Ala Ala Arg Pro Arg Trp Arg
        20                  25
```

(2) INFORMATION FOR SEQ ID NO: 15:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 15:

```
TCGCGACACT GCTCATCCCA GCCATCACGA CTGCTGACGC CGGCTTCTAC CTCTGCGTGG    60

CCACCAGCCC TGCAGGCACT GCC                                            83
```

(2) INFORMATION FOR SEQ ID NO: 16:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 16:

```
CGCATGAAGA AGAAGGATGA AGGCAGTTAC GACTTGGGCA AGAAACCCAT CTACAAAAAA    60

GCCCCCACCA ACGAGTTCTA CGCATGA                                        87
```

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 17:

```
Leu Gly Lys Lys Pro Ile Tyr Lys Lys
1               5
```

(2) INFORMATION FOR SEQ ID NO: 18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 18:

```
CCCCGCCAGC AAGAGCCGGA GCT                                            23
```

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 19:

```
GTGAGGCTCT GGGCGAGTGG GGG                                            23
```

(2) INFORMATION FOR SEQ ID NO: 20:

(i) SEQUENCE CHARACTERISTICS:
        (A) LENGTH: 33 base pairs (B) TYPE: nucleic acid
        (C) STRANDEDNESS: single
        (D) TOPOLOGY: linear (xi) SEQUENCE DESCRIPTION: SEQ ID NO: 20:

ATAGAGCTCT TGGAACCATG GCGCCTGTCT GCC                                33

(2) INFORMATION FOR SEQ ID NO: 21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 21:

GGAATTCCAG GTTTTATTAT CTTTTTATC                                    29

(2) INFORMATION FOR SEQ ID NO: 22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 22:

CGTATTGGGC GCCGTGTCAC CAGGGC                                       26

(2) INFORMATION FOR SEQ ID NO: 23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 23:

GGCCATGAGC TCCACCACCC TGTTCG                                       26

(2) INFORMATION FOR SEQ ID NO: 24:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 24:

Leu Gly Lys Lys Pro Ile Tyr Lys Lys
1               5

(2) INFORMATION FOR SEQ ID NO: 25:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 25:

Glu Phe Tyr Ala
1